United States Patent
Mathison et al.

[11] 3,953,458
[45] Apr. 27, 1976

[54] 1-SUBSTITUTED AMINO-2-ALKYL-5-HYDROXY-7,8-CYCLOPENTANO[H]-1,2,3,4-TETRAHYDROISOQUINOLINES

[75] Inventors: Ian William Mathison; William Ebenezer Solomons, both of Memphis, Tenn.; Raymond Henry Jones, Northport, N.Y.

[73] Assignee: Marion Laboratories, Inc., Kansas City, Mo.

[22] Filed: Mar. 28, 1974

[21] Appl. No.: 455,561

[52] U.S. Cl........................ 260/288 CF; 260/287 D; 260/289 R; 424/258
[51] Int. Cl.².................................. C07D 217/02
[58] Field of Search................ 260/288 CF, 240 G

[56] References Cited
OTHER PUBLICATIONS

Morrison et al., Organic Chemistry, 2nd Ed., (1969), p. 734.
Morrison et al., Organic Chemistry, 2nd Ed., (1969), p. 567.
Burger, Medicinal Chemistry, 2nd Ed., (1960), pp. 42 & 497.

*Primary Examiner*—R. Gallagher
*Assistant Examiner*—Diana G. Rivers
*Attorney, Agent, or Firm*—Merriam, Marshall, Shapiro & Klose

[57] ABSTRACT

2-Alkyl-7,8-cyclopentano[h]-1,2,3,4-tetrahydroisoquinolines of the formula

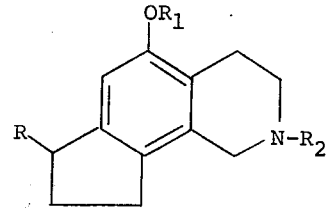

wherein R is an aryl-lower alkyl amino group, an aryl-lower alkyl imino group, a diaryl-lower alkyl amino group or a diaryl-lower alkyl imino group, $R_1$ is hydrogen or a lower alkyl group and $R_2$ is a lower alkyl group, and acid addition salts and quaternary ammonium salts thereof, and the use of such compounds in pharmaceutical compositions to lower blood pressure in hypertensive animals.

13 Claims, No Drawings

1-SUBSTITUTED AMINO-2-ALKYL-5-HYDROXY-7,8-CYCLOPENTANO[H]-1,2,3,4-TETRAHYDROISOQUINOLINES

This invention relates to novel chemical compounds and their production. More particularly, this invention provides novel tetrahydroisoquinolines, processes for producing the compounds, novel intermediates useful in making the compounds, and novel pharmaceutical compositions containing the compounds useful for effecting desirable pharmacological activity in animals.

According to one aspect of the subject invention there is provided novel 2-alkyl-7,8-cyclopentano[h]-1,2,3,4-tetrahydroisoquinolines of the formula oxy, ethoxy, propoxy, isopropoxy, butoxy, sec-butoxy, amyloxy and hexyloxy.

The term "aryl" as used herein includes the phenyl group and phenyl groups having 1 to 3 substituents such as lower alkyl groups, lower alkoxy groups, halo groups such as the bromo, chloro and fluoro groups, the nitro group, the hydroxy group, the methylenedioxy group and the trifluoromethyl group.

According to one aspect of the invention, 5-lower alkoxy-2-lower alkyl-7,8-cyclopentano[h]-1,2,3,4-tetrahydroisoquinoline-1'-ones can be reacted with an aryl-lower alkyl amine or a diaryl-lower alkyl amine to form an intermediate imine, the imine can then be reduced to form an amine and the resulting 5-lower alkoxy compound can be subjected to ether cleavage conditions to form a 5-hydroxy compound. This sequence of reactions can be represented as follows:

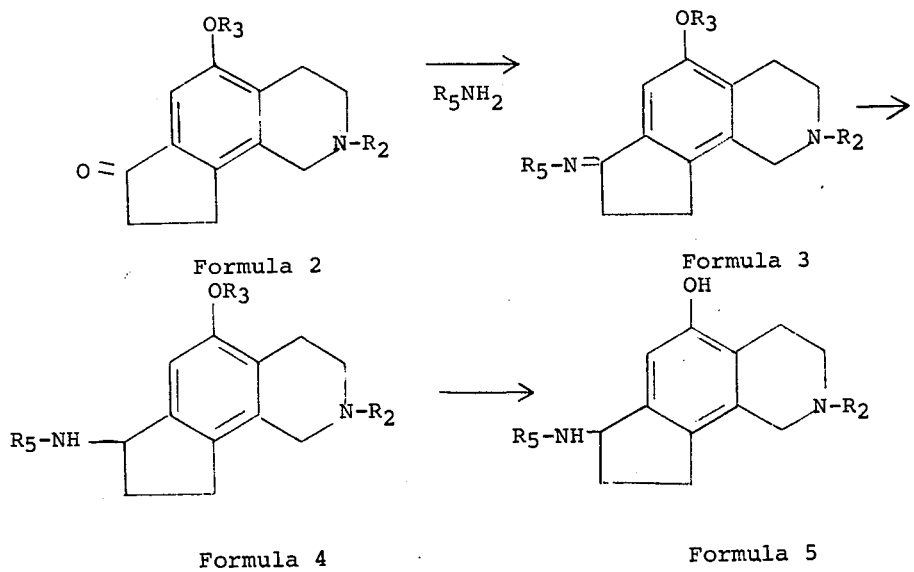

Formula 2

Formula 3

Formula 4

Formula 5

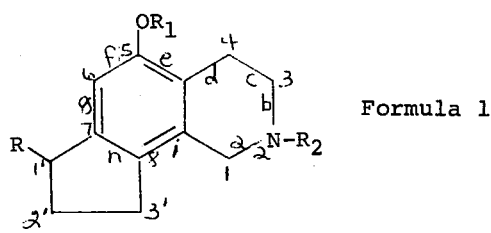

Formula 1 wherein R is an aryl-lower alkyl amino group, an aryl-lower alkyl imino group, a diaryl-lower alkyl amino group or a diaryl-lower alkyl imino group, $R_1$ is hydrogen or a lower alkyl group and $R_2$ is a lower alkyl group, and acid addition salts and quaternary ammonium salts thereof.

As used herein, the term "lower alkyl" means saturated monovalent aliphatic radicals, including straight and branched-chain groups, of from 1 to 8, and advisably 1 to 6, carbon atoms, including but not limited to methyl, ethyl, propyl, isopropyl, butyl, sec-butyl, amyl and hexyl.

The term "lower alkoxy" as used herein means saturated monovalent radicals, including straight and branched-chain groups, of from 1 to 8, and advisably 1 to 6, carbon atoms, including but not limited to methwherein $R_2$ and $R_3$ are each lower alkyl groups and $R_5$ is an aryl-lower alkyl group or a diaryl-lower alkyl group.

Some of the starting materials (Formula 2) which can be used in the process are 5-methoxy-2-methyl-7,8-cyclopentano[h]-1,2,3,4-tetrahydroisoquinoline-1'-one, 5-ethoxy-2-ethyl-7,8-cyclopentano[h]-1,2,3,4-tetrahydroisoquinoline-1'-one, 5-propoxy-2-propyl-7,8-cyclopentano[h]-1,2,3,4-tetrahydroisaquinoline-1'-one and 5-methoxy-2-ethyl-7,8-cyclopentano[h]-1,2,3,4-tetrahydroisoquinoline-1'-one.

Some of the aryl-lower alkyl amines and diaryl-lower alkyl amines which can be used in the process are benzylamine, phenylethylamine, phenylpropylamine, phenylisopropylamine, diphenylmethylamine, 2,2-diphenylethylamine, 3,3-diphenylpropylamine, 5,5-diphenylamylamine and 2,2-diphenyl-1-methylethylamine. Such amines having one to three substituents on the aryl ring such as lower alkoxy, lower alkyl, halo, nitro, trifluoromethyl and hydroxy groups can also be used, including 3,4-dimethoxyphenethylamine, p-chlorobenzylamine, p-methylphenylisopropylamine, 3,4,5-trimethoxybenzylamine and p-(trifluoromethyl)-phenylpropylamine.

Formation of the imine can be effected by combining a 5-lower alkoxy-2-lower alkyl-7,8-cyclopentano[h]-1,2,3,4-tetrahydroisoquinoline-1'-one and an aryl-lower alkyl amine, or a diaryl-lower alkyl amine, in a suitable liquid reaction medium, such as benzene, in the presence of a small amount of acid with heating at reflux temperature. The resulting imine can be recovered from the reaction mixture and be purified or it can be reduced directly without purification by catalytic hydrogenation using platinum oxide and a moderate pressure of about 20 to 100 psig at room temperature in glacial acetic acid. After hydrogen uptake has ceased the amine can be recovered by conventional methods.

Some of the imines (Formula 3) which can be produced as described are 1'-benzylimino-5-methoxy-2-ethyl-7,8-cyclopentano[h]-1,2,3,4-tetrahydroisoquinoline, 1'-phenethylimino-5-ethoxy-2-ethyl-7,8-cyclopentano[h]-1,2,3,4-tetrahydroisoquinoline, 1'-phenylisopropylimino-5-propoxy-2-amyl-7,8-cyclopentano[h]-1,2,3,4-tetrahyroisoquinoline, 1'-(3,4-dimethoxybenzylimino)-5-methoxy-2-ethyl-7,8-cyclopentano[h]-1,2,3,4-tetrahydroisoquinoline, 1'-(p-trifluoromethylphenylethylimino)-5-ethoxy-2-propyl-7,8-cyclopentano[h]-1,2,3,4-tetrahydroisoquinoline, 1'-(diphenylmethylimino)-5-methoxy-2-methyl-7,8-cyclopentano[h]-1,2,3,4-tetrahydroisoquinoline, 1'-(2,2-diphenylethylimino)-5-ethoxy-2-ethyl-7,8-cyclopentano[h]-1,2,3,4-tetrahydroisoquinoline, 1'-(3,3-diphenylpropylimino-5-propoxy-2-amyl-7,8-cyclopentano[h]-1,2,3,4-tetrahydroisoquinoline, 1'-(5,5-diphenylamylimino)-5-butoxy-2-ethyl-7,8-cyclopentano[h]-1,2,3,4-tetrahydroisoquinoline and 1'-(2,2-diphenyl-1-methylethylimino)-5-lower alkoxy-2-propyl-7,8-cyclopentano[h]-1,2,3,4-tetrahydroisoquinoline.

Representative of amines (Formula 4) which can be produced as described are 1'-benzylamino-5-methoxy-2-methyl-7,8-cyclopentano[h]-1,2,3,4-tetrahydroisoquinoline, 1'-phenethylamino-5-ethoxy-2-ethyl-7,8-cyclopentano[h]-1,2,3,4-tetrahydroisoquinoline, 1'-phenylisopropylamino-5-propoxy-2-amyl-7,8-cyclopentano[h]-1,2,3,4-tetrahydroisoquinoline, 1'-(3,4-dimethoxybenzylamino)-5-methoxy-2-ethyl-7,8-cyclopentano[h]-1,2,3,4-tetrahydroisoquinoline, 1'-(p-trifluoromethylphenylethylamino)-5-ethoxy-2-propyl-7,8-cyclopentano[h]-1,2,3,4-tetrahydroisoquinoline, 1'-(diphenylmethylamino)-5-methoxy-2-methyl-7,8-cyclopentano[h]-1,2,3,4-tetrahydroisoquinoline, 1'-(2,2-diphenylethylamino-5-ethoxy-2-ethyl-7,8-cyclopentano[h]-1,2,3,4-tetrahydroisoquinoline, 1'-(3,3-diphenylpropylamino)-5-propoxy-2-amyl-7,8-cyclopentano[h]-1,2,3,4-tetrahydroisoquinoline, 1'-(5,5-diphenylamylamino)-5-butoxy-2-ethyl-7,8-cyclopentano[h]-1,2,3,4-tetrahydroisoquinoline and 1'-(2,2-diphenyl-1-methylethylamino)-5-lower alkoxy-2-propyl-7,8-cyclopentano[h]-1,2,3,4-tetrahydroisoquinoline.

In the next step of the process the 5-lower alkoxy group and any other similar ether groups present on the aryl or di-aryl substituent can be cleaved and a hydroxy group introduced in place thereof. Specifically, 48% hydrobromic acid can be used for cleaving the 5-lower alkoxy ether group.

Representative of the 5-hydroxy compounds (Formula 5) which are produced as described are 1'-benzylamino-5-hydroxy-2-methyl-7,8-cyclopentano[h]-1,2,3,4-tetrahydroisoquinoline, 1'-phenethylamino-5-hydroxy-2-ethyl-7,8-cyclopentano[h]-1,2,3,4-tetrahydroisoquinoline, 1'-phenylisopropylamino-5-hydroxy-2-amyl-7,8-cyclopentano[h]-1,2,3,4-tetrahydroisoquinoline, 1'-(3,4-dihydroxybenzylamino)-5-hydroxy-2-ethyl-7,8-cyclopentano[h]-1,2,3,4-tetrahydroisoquinoline, 1'-(p-trifluoromethylphenylethylamino)-5-hydroxy-2-propyl-7,8-cyclopentano[h]-1,2,3,4-tetrahydroisoquinoline, 1'-(diphenylmethylamino)-5-hydroxy-2-methyl-7,8-cyclopentano[h]-1,2,3,4-tetrahydroisoquinoline, 1'-(2,2-diphenylethylamino)-5-hydroxy-2-ethyl-7,8-cyclopentano[h]-1,2,3,4-tetrahydroisoquinoline, 1'-(3,3-diphenylpropylamino)-5-hydroxy-2-amyl-7,8-cyclopentano[h]-1,2,3,4-tetrahydroisoquinoline, 1'-(5,5-diphenylamylamino)-5-hydroxy-2-ethyl-7,8-cyclopentano[h]-1,2,3,4-tetrahydroisoquinoline and 1'-(2,2-diphenyl-1-methylethylamino)-5-hydroxy-2-propyl-7,8-cyclopentano[h]-1,2,3,4-tetrahydroisoquinoline.

The tertiary amines, can be converted to acid addition salts by contacting the amines with a suitable inorganic acid such as hydrochloric acid, sulfuric acid, phosphoric acid and hydrobromic acid or an organic acid such as citric acid, acetic acid, formic acid, malic acid, fumaric acid, succinic acid, benzoic acid and tartaric acid.

Quaternary ammonium salts of the compounds are readily prepared by contacting the compounds with an alkyl halide or an alkyl sulfate, aralkyl halide or aralkyl sulfate such as methyl chloride, ethyl bromide, propyl iodide, benzyl sulfate and methyl sulfate as well as other compounds known to form quaternary ammonium salts with tertiary amines.

The compounds of this invention are useful as neutralizing agents since they are bases which form salts with acids.

According to a second aspect of the invention, the nontoxic compounds of this invention are also useful pharmaceutically. These compounds when administered to animals parenterally or orally exert anti-hypertensive effect. The compounds thus can be used to reduce blood pressure.

1'-(3,4-dimethoxyphenethylamino)-5-methoxy-2-methyl-7,8-cyclopentano[h]-1,2,3,4-tetrahydroisoquinoline as the base administered as a solution in distilled water has an $ALD_{50}$ in mice of 100–200 mg./kg. i.p. When administered as the base, in an aqueous suspension in 1% gum tragacanth, at 50 mg./kg. i.p. to hypertensive rats the following percent change in systolic blood pressure was observed:

| 1 Hour | −12.0 ± 3.8 |
| 2 Hours | − 8.7 ± 3.7 |
| 4 Hours | − 7.4 ± 2.5 |
| 24 Hours | − 7.9 ± 1.4 |

1'-(3,4-Dihydroxyphenethylamino)-5-hydroxy-2-methyl-7,8-cyclopentano[h]-1,2,3,4-tetrahydroisoquinoline as the base administered as a solution in distilled water has an $ALD_{50}$ in mice of 100–141 mg./kg. i.p. When administered as the base, as a solution in distilled water, at 25 mg./kg. i.p. to hypertensive rats the following change in systolic blood pressure was observed:

| 1 Hour | − 5.7 ± 2.3 |
| 2 Hours | −11.7 ± 4.8 |
| 4 Hours | −12.0 ± 3.8 |
| 24 Hours | −10.8 ± 3.0 |

The amount of active ingredient administered may be varied; however, it is necessary that the amount of active ingredient be such that a suitable dosage is given. The selected dosage depends upon the desired therapeutic effect and on the duration of treatment. Dosages of from 0.1 to 25 mg./kg. of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg. of active agent.

A typical tablet can have the composition:

|  | Mg |
|---|---|
| Active agent (1) | 100 |
| Starch U.S.P. | 57 |
| Lactose U.S.P. | 73 |
| Talc. U.S.P. | 9 |
| Stearic acid | 12 |

(1) 1'-(3,4-dihydroxyphenethylamino)-5-hydroxy-2-methyl-7,8-cyclopentano[h]-1,2,3,4-tetrahydroisoquinoline The compounds of the invention are both orally and parenterally active and accordingly they can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art, such as water. Besides inert diluents, such preparations can also include adjuvants such as wetting agents, emulsifying and suspending agents and sweetening, flavoring and perfuming agents.

Preparation for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

Preparation of Starting Materials Used in This Invention

The 5-lower alkoxy-2-lower alkyl-7,8-cyclopentano[h]-1,2,3,4-tetrahydroisoquinoline-1'-ones used as starting materials in this invention can be produced by converting a 5-alkoxy-2-alkyl-1,2,3,4-tetrahydroisoquinoline by means of a Friedal-Crafts reaction to a 5-alkoxy-2-alkyl-1,2,3,4-tetrahydroisoquinoline-8-carboxyaldehyde, reacting the aldehyde with malonic acid to form a β-(5-alkoxy-2-alkyl-1,2,3,4-tetrahydroisoquinoline-8)proenoic acid, catalytically reducing the propenoic acid compound to form the β-(5-alkoxy-2-alkyl-1,2,3,4-tetrahydroisoquinoline-8)propanoic acid and then effecting ring closure of such compound by means of polyphosphoric acid. This process can be represented as follows:

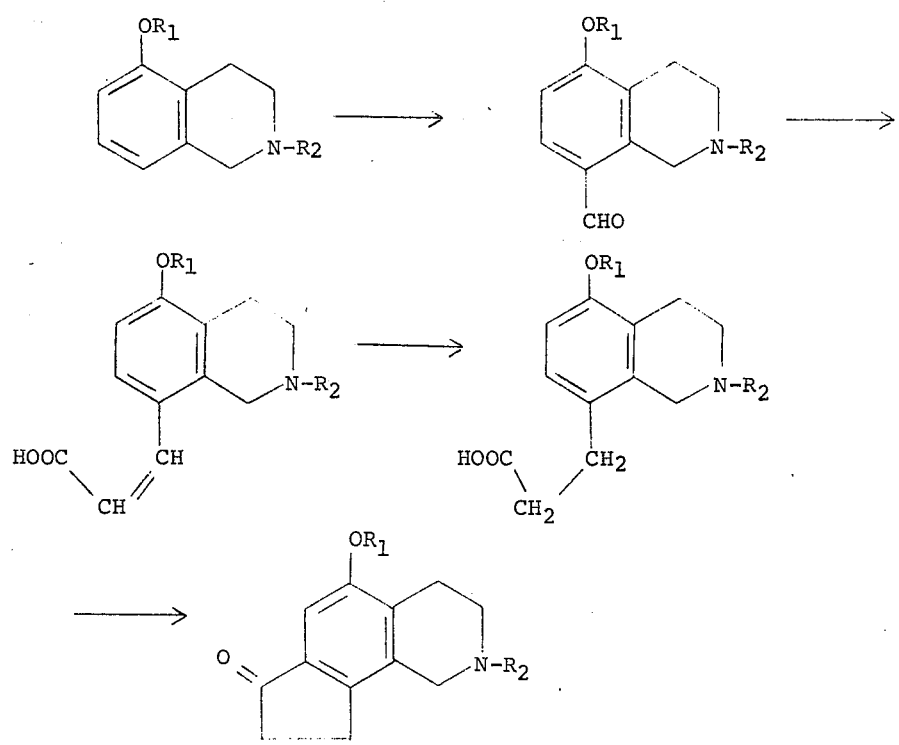

wherein $R_1$ and $R_2$ are the same or different lower alkyl groups.

Among the 5-alkoxy-2-alkyl-1,2,3,4-tetrahydroisoquinolines which can be used in the process as starting materials are 5-methoxy- 2-methyl-1,2,3,4-tetrahydroisoquinoline, 5-methoxy-2-ethyl-1,2,3,4-tetrahydroisoquinoline, 5-ethoxy-2-ethyl-1,2,3,4-tetrahydroisoquinoline and 5-propoxy-2-propyl-1,2,3,4-tetrahydroisoquinoline. Durand et al., *Bull. Soc. Chim France*, 270 (1961) discloses the preparation of 5-methoxy-2-methyl-1,2,3,4-tetrahydroisoquinoline. Other such compounds, including those just named, can be prepared by the same process from the appropriate reactants. In addition, the preparation of the starting materials is well within the ordinary skill of an organic chemist.

Formylation of the 5-alkoxy-2-alkyl-1,2,3,4-tetrahydroisoquinoline starting material is readily effected according to the method of Alfred Reiche et al. in *Chem. Ber.*, 93, 88 (1960) using a Friedel-Crafts catalyst such as stannic tetrachloride, aluminum trichloride or titanium tetrachloride and α,α-dichloromethyl methyl ether followed by the addition of water. Some of the novel products which are produced as described are 5-methoxy-2-methyl-1,2,3,4-tetrahydroisoquinoline-8-carboxyaldehyde, 5-methoxy-2-ethyl-1,2,3,4-tetrahydroisoquinoline-8-carboxaldehyde, 5-ethoxy-2-ethyl-1,2,3,4-tetrahydroisoquinoline-8-carboxaldehyde and 5-propoxy-2-propyl-1,2,3,4-tetrahydroisoquinoline-8-carboxaldehyde.

Conversion of the 5-alkoxy-2-alkyl-1,2,3,4-tetrahydroisoquinoline-8-carboxaldehyde by reaction with malonic acid in pyridine in the presence of piperidine as a catalyst at an elevated temperature, according to the Doebner modification of the Perkin reaction (Johnson "Organic Reactions" Vol. I, 226–234, John Wiley & Sons, N.Y. 1942) yields β-(5-alkoxy-2-alkyl-1,2,3,4-tetrahydroisoquinoline-8)propenoic acid. Among the compounds which are produced in this way are β-(5-methoxy-2-methyl-1,2,3,4-tetrahydroisoquinoline-8)propenoic acid, β-(5-methoxy-2-ethyl-1,2,3,4-tetrahydroisoquinoline-8)propenoic acid, β-( 5-ethoxy-2-ethyl-1,2,3,4-tetrahydroisoquinoline-8)propenoic acid and β-(5-propoxy-2-propyl-1,2,3,4-tetrahydroisoquinoline-8)propenoic acid.

Reduction of the unsaturated vinyl linkage in the propenoic acids is readily effected catalytically with hydrogen using palladium as the catalyst in a suitable inert liquid reaction medium containing a small amount of an acid. The hydrogenation proceeds at room temperature. After hydrogen uptake has ceased the desired β-(5-alkoxy-2-alkyl-1,2,3,4-tetrahydroisoquinoline-8) propanoic acid can be recovered by conventional methods. Among the compounds which can be produced in this way are β-(5-methoxy-2-methyl-1,2,3,4-tetrahydroisoquinoline-8) propanoic acid, β-(5-ethoxy-2-ethyl-1,2,3,4-tetrahydroisoquinoline-8) propanoic acid, β-(5-propoxy-2-propyl-1,2,3,4-tetrahydroisoquinoline-8) propanoic acid and β-(5-methoxy-2-ethyl-1,2,3,4-tetrahydroisoquinoline-8) propanoic acid.

In the next step of the process the β-(5-alkoxy-2-alkyl-1,2,3,4-tetrahydroisoquinoline-8)propanoic acid is cyclized in polyphosphoric acid according to the method of Koo, *J. Am. Chem. Soc.* 75, 1891 (1953) to produce 5-alkoxy-2-alkyl-7,8-cyclopentano[h]-1,2,3,4-tetrahydroisoquinoline-1'-one. The reaction is effected at a moderately elevated temperature of about 60° to 80°C. The desired product is isolated from the reaction mixture by the addition of water followed by extraction with a suitable solvent such as diethyl ether.

Among the products which are produced by the described cyclization are 5-methoxy-2-methyl-7,8-cyclopentano[h]-1,2,3,4-tetrahydroisoquinoline-1'-one, 5-ethoxy-2-ethyl-7,8-cyclopentano[h]-1,2,3,4-tetrahydroisoquinoline-1'-one, 5-propoxy-2-propyl-7,8-cyclopentano[h]-1,2,3,4-tetrahydroisoquinoline-1'-one and 5-methoxy-2-ethyl-7,8-cyclopentano[h]-1,2,3,4-tetrahydroisoquinoline-1'-one.

Examples 5 to 8 illustrate specifically the preparation of one such starting material by the described process.

The following examples are presented to illustrate, but not limit, the invention.

EXAMPLE 1

1'-(3,4-dimethoxyphenethylamino)-5-methoxy-2-methyl-7,8-cyclopentano[h]-1,2,3,4-tetrahydroisoquinoline dihydrobromide Into a flask (100 ml.) were placed 5-methoxy-2-methyl-7,8-cyclopentano[h]-1,2,3,4-tetrahydroisoquinoline-1'-one (1.0 g., 0.00427 mole), 3,4-dimethoxyphenethylamine (0.78 g., 0.00427 mole), dry benzene (60 ml.) and glacial acetic acid (4 drops). The flask was attached to a Dean-Stark trap and the reaction mixture was refluxed for 96 hours. The reaction was not complete as evidenced by ir absorption at 1690 cm$^{-1}$ (C=O), but additional refluxing failed to yield more product, indicated by ir absorption at 1645 cm$^{-1}$ (C=N). The solvent was removed and the residue was agitated in diethyl ether (50 ml.), then collected by filtration. The crude 1'-(3,4-dimethoxyphenethylamino)-5-methoxy-2-methyl-7,8-cyclopentano[h]-1,2,3,4-tetrahydroisoquinoline, m.p. 130°–133°C. (1.2 g., 67%), was dissolved in glacial acetic acid, and the solution was poured into an hydrogenation bottle containing 0.3 g. of platinum oxide and treated with hydrogen at 40 psi for 48 hrs. on a low pressure Parr hydrogenation apparatus. The solvent was removed from the filtrate leaving a residue which was dissolved in water and made basic. The product was extracted from the aqueous suspension with ether and the extract was dried over sodium sulfate. Hydrobromic acid was bubbled into the decanted extract resulting in formation of the dihydrobromide salt which was recrystallized from methanol, m.p. 266°–267°C. (0.76 g., 45%).

Anal. Calcd. for $C_{24}H_{34}N_2O_3Br_2$: C, 51.62; H, 6.15; N, 5.01; Br, 28.63.

Found: C, 51.63; H, 6.08; N, 4.94; Br, 28.40.

EXAMPLE 2

1'-(2,2-Diphenethylamino-5-methoxy-2-methyl-7,8-cyclopentano[h]-1,2,3,4-tetrahydroisoquinoline Into a flask (100 ml.) were placed 5-methoxy- 2-methyl-7,8-cyclopentano[h]-1,2,3,4-tetrahydroisoquinoline-1'-one, (1.0 g., 0.00427 mole), 2,2-diphenthylamine (0.85 g., 0.00427 mole), dry benzene (60 ml.) and glacial acetic acid (5 drops). The flask was attached to a Dean-Stark trap and the solution was refluxed for 72 hrs.; this was followed by removal of the benzene and agitation of the residue in ether (50 ml.). The crude 1'-(2,2-diphenethylimino)-5-methoxy-2-methyl-7,8-cyclopentano[h]-1,2,3,4-tetrahydroisoquinoline, m.p. 151°–153°C. (1.4 g., 76%), was dissolved in glacial acetic acid and poured into an hydrogenation bottle containing 0.3 g. of platinum oxide. The reaction mixture was treated with hydrogen on a low pressure Paar hydrogenation apparatus for 24 hrs. After filtration, the solvent was removed from the filtrate and the residue was dissolved in water. The aqueous solution was made basic and extracted with ether followed by drying of the extract over sodium sulfate and removal of the ether. The residue was chromatographed on a silica gel column with ethanol. The purified product was a thick viscous oil (0.7 g., 50%) which did not boil below 200°C. at 0.1 mm-Hg.

Anal. Calcd. for $C_{28}H_{32}N_2O$: C, 81.50; H, 7.83; N, 6.79.

Found: C, 81.35; H, 8.13; N, 6.53.

EXAMPLE 3

1'-(3,4-Dihydroxyphenethylamino)-5-hydroxy-2-methyl-7,8-cyclopentano[h]-1,2,3,4-tetrahydroisoquinoline dihydrobromide Into a flask (100 ml.) were placed 1'-(3,4-dimethoxyphenethylamino)-5-methoxy-2-methyl-7,8-cyclopentano[h]-1,2,3,4-tetrahydroisoquinoline dihydrobromide, (1.2 g., 0.00215 mole) and concentrated (48%) hydrobromic acid (50 ml.). After the reaction mixture had refluxed gently for 3 hrs., the excess hydrogen bromide was removed on a solvent evaporator and the residue was recrystallized from methanol, m.p. 243°–244°C. (0.7 g., 58%).

Anal. Calcd. for $C_{21}H_{28}N_2O_3Br_2$: C, 48.85; H, 5.48; N, 5.42; Br, 30.95.

Found : C, 48.55; H, 5.33; N, 5.25; Br, 30.71.

EXAMPLE 4

1'-Benzylimino-5-methoxy-2-methyl-7,8-cyclopentano[h]-1,2,3,4-tetrahydroisoquinoline Into a flask were placed 5-methoxy-2-methyl-7,8-cyclopentano[h]-1,2,3,4-tetrahydroisoquinoline-1'-one, (1.0 g., 0.00427 mole), benzylamine (0.46 g., 0.00427 mole), dry benzene (60 ml.) and glacial acetic acid (5 drops). The flask was attached to a Dean Stark trap and the solution was refluxed for 92 hrs. This was followed by removal of the solvent and agitation of the residue in ether (50 ml.). The imine (0.6 g., 41%) was collected by filtration and recrystallized from ether (m.p. 125°–126°C.).

Anal. Calcd. for $C_{21}H_{24}N_2O$: C, 78.70; H, 7.56; N, 8.74. Found: C, 78.87; H, 7.33; N, 8.74.

The Following Illustrate the Preparation of Starting Materials Used in the Invention

EXAMPLE 5

5-Methoxy-2-methyl-1,2,3,4-tetrahydroisoquinoline-8-carboxaldehyde

Into a flask equipped with a mechanical stirrer, an equilibrium addition funnel, and a condenser fitted with a calcium chloride drying tube, were placed methylene chloride (150 ml.) and 5-methoxy- 2-methyl-1,2,3,4-tetrahydroisoquinoline (15.0 g., 0.085 mole). The solution was cooled to 0°C. and stirred. Titanium tetrachloride (51.6 g., 0.272 mole) was added gradually, followed by the rapid dropwise addition of α,α-dichloromethyl methyl ether (9.8 g., 0.085 mole). After the reaction mixture was allowed to warm to room temperature, it was refluxed for 7 hrs. The titanium chloride complex of the product was decomposed with water and ice, and the resulting solution kept cool as it was made basic with excess sodium hydroxide (20%). The resulting suspension was extracted with chloroform. The extract was dried over sodium sulfate and the solvent removed, affording the crude product which was vacuum distilled (b.p. 122°C./0.1 mm.) to yield 13.0 g. (74%) of 5-methoxy-2-methyl-1,2,3,4-tetrahydroisoquinoline-8-carboxaldehyde. The hydrochloride salt melted at 244°–245°C. after recrystallization from absolute ethanol.

EXAMPLE 6

β-(5-Methoxy-2-methyl-1,2,3,4-tetrahydroisoquinoline-8)propenoic acid hydrochloride Into a flask (100 ml.). were placed malonic acid (12.0 g., 0.116 mole) and dry pyridine (25 ml.). The contents of the flask were heated until solution occurred. After the solution had cooled to room temperature, 5-methoxy-2-methyl-1,2,3,4-tetrahydroisoquinoline-8-carboxaldehyde (12.0 g., 0.058 mole) was added. Piperidine (25 drops) was added as a catalyst. The reaction mixture was warmed for 30 min. at 80°C. followed by a 2½ hr. refluxing. After the solution had cooled, it was poured into cold water (200 ml.) and slowly collected by filtration and dried (4 hrs., 110°C); it was then ground and further dried (2 hrs., 110°C.) in a vacuum oven. The filtrate was successively concentrated and cooled until no additional product precipitated. The β-(5-methoxy-2-methyl-1,2,3,4-tetrahydroisoquinoline-8)propenoic acid hydrochloride, m.p. 260°–265°C. (11.5 g., 70%) was not purified.

EXAMPLE 7

β-(5-Methoxy-2-methyl-1,2,3,4-tetrahydroisoquinoline-8)propanoic acid hydrochloride Into a hydrogenation bottle (500 ml.) were placed 5% palladium on charcoal (0.5 g.) and a suspension of β-(5-methoxy-2-methyl-1,2,3,4-tetrahydroisoquinoline-8)propenoic acid hydrochloride (5.7 g., 0.028 mole) in dilute (1%) hydrochloric acid (250 ml.). The compound was reduced with hydrogen during a 20 hr. period in a low pressure hydrogenation apparatus. After removal of the catalyst by filtration, the filtrate was successively concentrated and cooled until no further product precipitated. The portions of the product β-(5-methoxy-2-methyl-1,2,3,4-tetrahydroisoquinoline-8)propanoic acid hydrochloride were collected by filtration and dried (4 hrs., 110°C.) in a vacuum oven. If the dry product (4.8 g., 84%) had a melting point less than 210°C., it was recrystallized from water (m.p. 212°C.).

EXAMPLE 8

5-Methoxy-2-methyl-7,8-cyclopentano[h]-1,2,3,4-tetrahydroisoquinoline-1'-one

Into a flask (500 ml.) which was heated to 55°C. with an oil bath and equipped with a mechanical stirrer, calcium chloride drying tube, and a thermometer, were placed preheated (steam bath) polyphosphoric acid (PPA) (100 g.) and β-(5-methoxy-2-methyl-1,2,3,4-tetrahydroisoquinoline-8)propanoic acid (7.4 g., 0.026 mole). The mixture was stirred as the temperature of the oil bath was gradually raised. At an internal temperature of 60°C. the reaction commenced, as evidenced by a light green color. The internal temperature was raised to 78°C. over a 15 min. period and maintained there for a further 20 min. The reaction mixture became dark green during this time. The PPA complex formed was then decomposed with ice and water after the contents of the flask had cooled to room temperature. The solution was kept at room temperature or cooler during basification with sodium hydroxide (20%) by the addition of large amounts of ice. The resulting suspension was extracted with diethyl ether and the extract was dried over sodium sulfate. Removal of the ether afforded the crude product 5-methoxy-2-methyl-7,8-cyclopentano[h]-1,2,3,4-tetrahydroisoquinoline-1′-one which was recrystallized (m.p. 151°–152°C.) from diethyl ether (3.9 g., 65%).

The foregoing detailed description has been given for clearness of understanding only, and no unnecessary limitations should be understood therefrom, as modifications will be obvious to those skilled in the art.

What is claimed is:

1. A compound of the formula

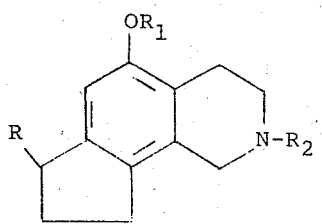

wherein R is a phenyl-lower alkyl amino, 3,4-dimethoxyphenyl-lower alkyl amino, 3,4-dihydroxyphenyl-lower alkyl amino, phenyl-lower alkyl imino, 3,4-dimethoxyphenyl-lower alkyl imino, 3,4-dihydroxyphenyl-lower alkyl imino, diphenyl-lower alkyl amino or diphenyl-lower alkyl imino group in which groups the lower alkyl has 1 to 8 carbon atoms, $R_1$ is hydrogen or a lower alkyl having 1 to 8 carbon atoms and $R_2$ is a lower alkyl group having 1 to 8 carbon atoms, and nontoxic acid addition salts thereof.

2. A compound according to claim 1 in which R is phenyl-lower alkyl amino phenyl-lower alkyl imino, $R_1$ is hydrogen or lower alkyl and $R_2$ is lower alkyl.

3. A compound according to claim 1 in which R is 3,4-dimethoxyphenyl-lower alkyl amino or 3,4-dimethoxyphenyl-lower alkyl imino, $R_1$ is lower alkyl and $R_2$ is lower alkyl.

4. A compound according to claim 1 in which R is 3,4-dihydroxyphenyl-lower alkyl amino or 3,4-dihydroxyphenyl-lower alkyl, $R_1$ is lower alkyl and $R_2$ is lower alkyl.

5. A compound according to claim 1 in which R is diphenyl-lower alkyl amino or diphenyl-lower alkyl imino, $R_1$ is lower alkyl and $R_2$ is lower alkyl.

6. The compound according to claim 3 named 1′-(3,4-dimethoxyphenethylamino)-5-methoxy-2-methyl-7,8-cyclopentano[h]-1,2,3,4-tetrahydroisoquinoline.

7. The compound according to claim 3 named 1′-(3,4-dimethoxyphenethylimino)-5-methoxy-2-methyl-7,8-cyclopentano[h]-1,2,3,4-tetrahydroisoquinoline.

8. The compound according to claim 5 named 1′-(2,2-diphenethylamino)-5-methoxy-2-methyl-7,8-cyclopentano[h]-1,2,3,4-tetrahydroisoquinoline.

9. The compound according to claim 5 named 1′-(2,2-diphenethylimino)-5-methoxy-2-methyl-7,8-cyclopentano[h]-1,2,3,4-tetrahydroisoquinoline.

10. The compound according to claim 4 named 1′-(3,4-dihydroxyphenethylamino-5-hydroxy-2-methyl-7,8-cyclopentano[h]-1,2,3,4-tetrahydroisoquinoline.

11. The compound according to claim 3 named 1′-benzylimino-5-methoxy-2-methyl-7,8-cyclopentano[h]-1,2,3,4-tetrahydroisoquinoline.

12. A compound of the formula

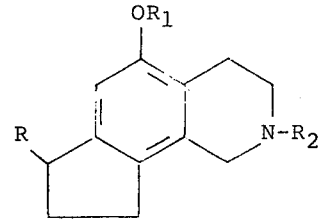

wherein R is a phenyl-lower alkyl amino, substituted phenyl-lower alkyl amino, phenyl-lower alkyl imino, substituted phenyl-lower alkyl imino, diphenyl-lower alkyl amino or substituted diphenyl-lower alkyl amino in which groups the lower alkyl has 1 to 8 carbon atoms and the substituted phenyl group have 1 to 3 lower alkyl, lower alkoxy, bromo, chloro, fluoro, nitro, hydroxy, methylenedioxy and trifluoromethyl groups with said lower alkyl and lower alkoxy groups having 1 to 8 carbon atoms, $R_1$ is hydrogen or a lower alkyl having 1 to 8 carbon atoms and $R_2$ is a lower alkyl group having 1 to 8 carbon atoms, and non-toxic acid addition salts and non-toxic quaternary ammonium salts thereof.

13. A compound of the formula

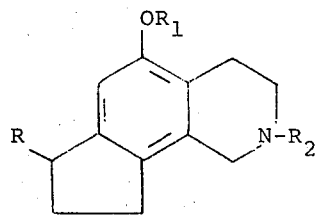

wherein R is a phenyl-lower alkyl amino group in which the phenyl has one to three nuclear lower alkoxy groups or one to three nuclear hydroxy groups, said lower alkyl and lower alkoxy groups having 1 to 8 carbon atoms, $R_1$ is hydrogen or lower alkyl having 1 to 8 carbon atoms and $R_2$ is a lower alkyl group having 1 to 8 carbon atoms, and nontoxic acid addition salts thereof.

* * * * *

UNITED STATES PATENT AND TRADEMARK OFFICE
CERTIFICATE OF CORRECTION

PATENT NO. : 3,953,458
DATED : April 27, 1976
INVENTOR(S) : Ian William Mathison et al.

It is certified that error appears in the above-identified patent and that said Letters Patent are hereby corrected as shown below:

In the title, change "1-Substituted" to --1'-Substituted--; column 2, line 52, change "tetrahydroisaquinoline" to --tetrahydroisoquinoline--; column 4, line 39, after "exert" insert --an--; column 6, line 37, change "proenoic" to --propenoic--; column 8, line 41, change "thylamino" to --thylimino--; column 9, line 2, change "diphenthylamine" to --diphenethylamine-- and in line 61, after "Following" insert --Examples--; column 11, line 52, after "amino" insert --or--; column 12, line 36, change "group" to --groups--.

Signed and Sealed this

Tenth Day of August 1976

[SEAL]

Attest:

RUTH C. MASON
Attesting Officer

C. MARSHALL DANN
Commissioner of Patents and Trademarks